United States Patent

Chu et al.

[11] Patent Number: 5,207,710
[45] Date of Patent: May 4, 1993

[54] METHOD FOR IMPROVING IMPLANT FIXATION

[75] Inventors: George H. Chu, Sunnyvale; Rosa Armstrong, Palo Alto; Robert Chang, Hillsborough, all of Calif.

[73] Assignee: Collagen Corporation, Palo Alto, Calif.

[21] Appl. No.: 819,059

[22] Filed: Jan. 10, 1992

Related U.S. Application Data

[60] Division of Ser. No. 527,765, May 23, 1990, which is a division of Ser. No. 275,215, Nov. 23, 1988, Pat. No. 5,108,436, which is a continuation-in-part of Ser. No. 250,952, Sep. 29, 1988, abandoned.

[51] Int. Cl.⁵ .......................... A61F 2/28; A61F 2/30
[52] U.S. Cl. ........................................ 623/16; 623/18
[58] Field of Search ........................ 623/16, 23

[56] References Cited

U.S. PATENT DOCUMENTS

| | | | |
|---|---|---|---|
| 3,929,971 | 12/1975 | Roy | 623/16 X |
| 4,356,572 | 11/1982 | Guillemin et al. | 623/16 X |
| 4,599,085 | 7/1986 | Riess et al. | 623/18 X |
| 4,774,228 | 9/1988 | Seyedin et al. | 623/16 X |
| 4,774,322 | 9/1988 | Seyedin et al. | 623/16 X |
| 4,863,732 | 9/1989 | Nathan et al. | 424/95 |
| 4,888,366 | 12/1989 | Chu et al. | 623/16 X |
| 4,968,590 | 11/1990 | Kuberasampath et al. | 530/326 |
| 4,976,736 | 12/1990 | White et al. | 623/16 |
| 5,001,169 | 3/1991 | Nathan et al. | 623/16 X |

FOREIGN PATENT DOCUMENTS 2564732  5/1985  France .
2164042  5/1985  United Kingdom .

*Primary Examiner*—Randall L. Green
*Assistant Examiner*—Dinh X. Nguyen
*Attorney, Agent, or Firm*—Morrison & Foerster

[57] ABSTRACT

Stress-bearing prostheses for replacement or partial replacement of stress-bearing bone are fixed in place by bony ingrowth by providing a stress-bearing member having a porous region in combination with an osteogenic factor extract or a purified osteogenic inductive protein, optionally in combination with a TGF-beta cofactor, in a pharmaceutically acceptable carrier. The carrier is preferably either a collagen composition or a ceramic.

12 Claims, 1 Drawing Sheet

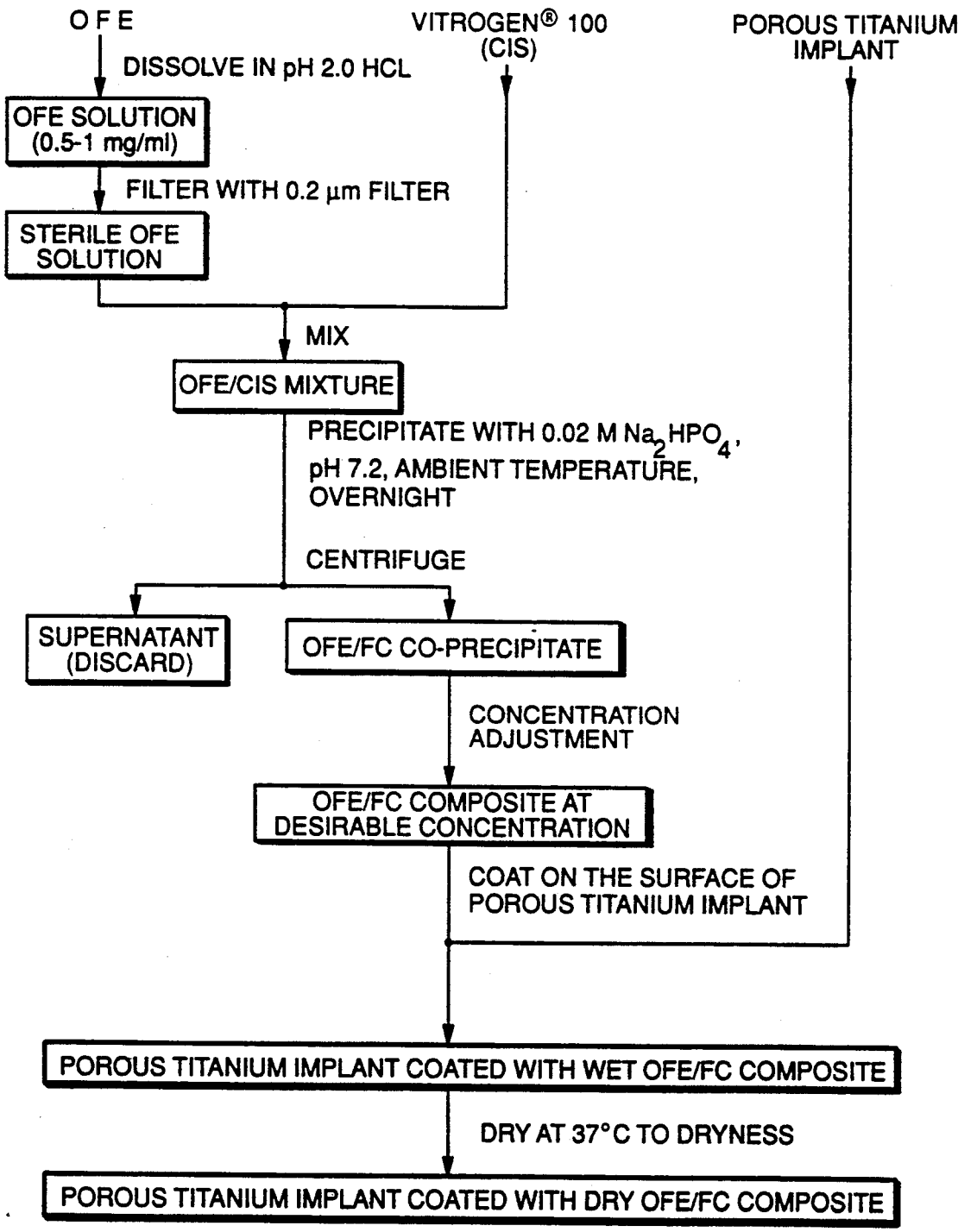
FIG._1

METHOD FOR IMPROVING IMPLANT FIXATION

CROSS REFERENCES

This application is a divisional application of co-pending U.S. patent application Ser. No. 07/527,765, filed May 23, 1990, abandoned, which is a divisional application of co-pending U.S. patent application Ser. No. 07/275,215, filed Nov. 23, 1988, now U.S. Pat. No. 5,108,436 which is a continuation-in-part of U.S. patent application Ser. No. 07/250,952, filed Sep. 29, 1988 (now abandoned), to which applications we claim priority under 35 USC §120 and which applications are incorporated herein by reference.

TECHNICAL FIELD

This invention relates to the field of stress-bearing bone replacements, and methods for permanent attachment of such replacements to the site of a bone defect. In particular, this invention relates to the use of purified bone proteins to induce bony ingrowth of a porous stress-bearing implant and fixation of the porous implant to the treatment site.

BACKGROUND ART

The use of stress-bearing materials for bone replacement is well known. A large number of designs have been used to replace missing or diseased portions of the bone structure which are stress-bearing, such as bone shafts, joints, and tooth roots. These designs include artificial shafts, joints, and associated devices intended to mimic the functions of the human skeletal system. The designs can be quite elaborate. See, for example, U.S. Pat. No. 3,820,167 which disclosed a design for an artificial hip joint.

Shafts and other prostheses for use as the stress-bearing portion of the bone replacement are typically constructed of metal or metal alloys. Such metal pins or artificial joints are constructed of suitable inert metals such as titanium, stainless steels, or alloys of metals such as cobalt, chromium and molybdenum. The metallic pin or joint is sometimes provided with an oxide coating in order to prevent corrosion and instability.

It has been observed in the use of such metallic implants that it is frequently necessary to provide a mechanism to fix its position with respect to adjacent bone and prevent it from shifting in place. Attempts have been made to provide this fixation using a cement. USSR patent application 733,665 published May 15, 1980, discloses an implant-fixing cement comprising a mixture of cartilage, collagen (of unspecified origin), and the patient's blood, which is used to secure an implanted pin in place.

Coating a prosthesis with a material ("bioglass") which purportedly encourages bone growth, thus securing the implant with the ingrowth, was disclosed in French Application Publication No 2,383,656, published Oct. 13, 1978. It has also been attempted to use wire mesh surrounding the stress-bearing member of the prosthesis to provide sufficient flexibility to obtain a firm fit, in some cases aided by additional metal strips (e.g., EPO Publication 071,242, published Feb. 9, 1983). In connection with this mesh, a biodegradable, biocompatible material (for example, collagen of unspecified origin) is employed, apparently to prevent damage to the wire mesh during insertion of the implant. The resulting implant is eventually secured by additional bone growth. Indeed, research has consistently shown that prostheses which have porous metal or porous ceramic surfaces are better secured by bony growth into the porous surface.

An attempt has been made to stimulate this bony ingrowth by providing a bone particle coating. U.S. Pat. No. 3,918,100 describes prostheses made of various metals which are coated using RF sputtering with bone particles in a vacuum. In this disclosure, aluminum oxide substrates are coated with a powder made of lye-treated bone chips. The coated prostheses are said to encourage living bone to grow onto the implant, and the coating finally to be absorbed by the surrounding tissue.

None of the foregoing achieves a satisfactory solution. The materials used are often immunogenic and incapable of inducing or stimulating surrounding bone growth at a sufficient rate to prevent damage due to shifting of the prostheses. The present invention provides prostheses which simulate the ingrowth of bone at sufficient rates to obtain a more satisfactory result.

DISCLOSURE OF THE INVENTION

An implanted stress-bearing prosthesis should be provided with a means to assure permanent attachment of the prosthesis to the remaining portions of the skeletal system; ideally, it should be provided with means which induces the surrounding bone to intrude into the porous surface of the implant, thus fixing the implant in place. The present invention provides an effective prosthesis which induces bone growth at a rate sufficient to provide rapid fixation.

One aspect of the invention is a prosthesis for implantation as a bone replacement (or partial replacement) which comprises a stress-bearing member combined with an effective amount of an osteogenic factor extract (OFE) in a pharmaceutically acceptable carrier.

Another aspect of the invention is a prosthesis for implantation as bone-replacement which comprises a stress-bearing member combined with a substantially pure osteogenically active protein and an effective amount of TGF-beta (transformation growth factor of the beta-type), combined with a pharmaceutically acceptable carrier.

Another aspect of the invention is a method for permanent fixation of a stress-bearing prosthesis by inducing bony ingrowth into the stress-bearing member by administration of an effective amount of an OFE in a pharmaceutically effective carrier.

Another aspect of the invention is a method for permanent fixation of a stress-bearing prosthesis by inducing bony ingrowth into the stress-bearing member by administration of a substantially pure osteogenically active protein and an effective amount of TGF-beta, combined with a pharmaceutically acceptable carrier.

Another aspect of the invention is a method for repairing bone defects which comprises administering a bone replacement composition comprising a stress-bearing member in combination with an effective amount of an OFE in a pharmaceutically acceptable carrier.

Another aspect of the invention is a method for repairing a bone defect which comprises administering a bone replacement composition comprising a stress-bearing member in combination with a substantially pure osteogenically active protein and an effective amount of TGF-beta, combined with a pharmaceutically acceptable carrier.

Another aspect of the invention is a process for preparing a stress-bearing prosthesis of the invention.

BRIEF DESCRIPTION OF THE DRAWING

FIG. 1 is a flow chart of the process for preparing a prosthesis of the invention as described in Paragraph B.1.

MODES OF CARRYING OUT THE INVENTION

A.1. The Stress-Bearing Member of the Prosthesis

The prosthesis of the invention comprises a stress-bearing member in combination with sterile, non-immunogenic osteogenically effective protein(s) in a pharmaceutically acceptable carrier. The stress-bearing member per se does not constitute the invention, and any conventionally used or operable stress-bearing prosthesis can be used. Such prostheses are typically metallic or ceramic, and are provided with porous surfaces by suitable techniques known in the art. The stress-bearing members themselves range from simple pins used to replace bone shaft portions, to fairly complex artificial joints and artificial tooth roots. These members may be made of ceramic, metal, transplanted replacement bone, and the like. They are of such design and material as to be appropriate to their intended use which may include replacement of diseased bone, correction of defects, or anchoring teeth. The term "stress-bearing member" as used herein refers to the generally rigid, structural component of the prosthesis of the invention. A stress-bearing member should be capable of withstanding the physical stress (e.g., torsion, compression, and the like) to which the natural bone it replaces is normally subject.

The stress-bearing members used in the invention preferably have porous regions where bony ingrowth is desired. For example, an artificial hip joint will typically comprise a smooth ball and socket joint which replaces the head of the femur and the pelvic socket, having metal posts for fixation in the pelvis and femur shaft. In such an implant, the posts would be provided with pores, either as a porous surface layer or as pores passing through the entire post, while other surfaces of the implant would be smooth (e.g., the joint faces, non-fixed portions of the artificial femur head, etc.). Thus, a "porous stress-bearing member" as used herein will have pores in at least a portion of the member.

A.2. Osteoinductive Component of the Prosthesis

Crude extracts containing proteins that exhibit osteoinductive activity and which meet the criterion of sufficient purity to be hypo-immunogenic in xenogeneic hosts may be prepared in several ways.

The native sources of the bone-inducing protein of the claimed invention are bone, dentin, osteosarcomas, and chondrosarcomas. In view of the fact that bone inductive proteins from human, monkey, bovine and rat are non-species specific in their ability to produce endochondral bone in xenogeneic implants (T. K. Sampath et al, *Proc Natl Acad Sci USA* (1983) 80:6591), it is believed that the protein of the claimed invention has been highly conserved among mammalian species (i.e., proteins from different mammalian species will have substantially homologous amino acid sequences that vary, if at all, in one or more amino acid residue additions, deletions, or substitutions that do not affect the non-species specific bone-inducing activity of the molecule adversely). In this regard the terms "substantially equivalent" and "substantially homologous" as used herein are intended to mean proteins, regardless of species of origin, that have the same amino acid composition or sequence as the protein described herein, and proteins of similar but different amino acid composition or sequence, which difference(s) does not affect non-species specific endochondral bone-inducing activity adversely. Accordingly, such proteins may be derived from cells or tissue of diverse mammalian origin. The source of protein prepared by purification from native sources is advantageously porcine or bovine long bone, because of its ready availability.

In a preferred embodiment, a partially purified bone-inducing protein is obtained from demineralized bone (DMB), as described in U.S. Pat. No. 4,627,982, incorporated herein by reference. Briefly, the purification method involves:

(1) extracting demineralized bone with a chaotropic (dissociative) extractant that solubilizes nonfibrous proteins;

(2) subjecting the extract to gel filtration to recover a fraction containing proteins of molecular weight 20,000–36,000 daltons (20–36 Kd);

(3) adsorbing the recovered fraction onto a carboxymethyl cellulose cation exchanger at approximately pH 4.5–5.5; and (4) eluting an osteogenically active fraction from the cation exchanger with a sodium chloride gradient of about 10 mM to about 150 mM.

The resulting osteogenic factor extract (OFE) may be used in this invention in amounts that effectively induce bony ingrowth into the stress-bearing member of the prosthesis ("osteogenically effective amount"). In general, the weight ratio of OFE to carrier used in the method of the invention will be in the range of about 1:5 to 1:100. The final composition of the invention will preferably contain approximately 50–200 $\mu$g OFE/cm$^2$ surface area of implant, and most preferably about 100 $\mu$g/cm$^2$.

In another preferred embodiment, the extract described above may be further purified by subjecting the 10 mM–150 mM NaCl fraction to reverse-phase high pressure liquid chromatography (RP-HPLC) or to non-denaturing gel electrophoresis. The protein is characterized as having a molecular weight (in its glycosylated state) of approximately 20–28 Kd as determined by SDS-PAGE analysis, and a partial amino acid internal sequence in the N-terminal half of the protein as follows:

- Lys-Tyr-Asn-Lys-Ile-Lys-Ser-Arg-Gly-Ile-Lys-Ala-Asn-Thr-Phe-Lys-Lys-Leu-His-Asn-Leu-Ser-Phe- X -Tyr-Thr-Asp-His-Asn-Ala-Leu-Gluwhere X represents an unspecified amino acid. The term "OIP" as used herein includes this osteoinductive protein, and substantially pure proteins that are substantially equivalent and substantially homologous thereto. The term "substantially pure" intends a composition containing less than about 30% by weight contaminating nonosteogenic protein, preferably less than about 10% by weight contaminating nonosteogenic protein, and most preferably less than about 5% by weight contaminating nonosteogenic protein. The term "substantially pure" is used relative to proteins with which the proteins are associated in nature and is not intended to exclude compositions in which the osteogenic proteins are admixed with proteinaceous or nonproteinaceous pharmaceutical carriers or vehicles. The invention also provides the osteogenic protein in novel partially glycosylated or completely nonglycosylated form.

A method for isolating purified OIP may be briefly described as follows:

(1) adsorbing the 10 mM-150 mM NaCl fraction described above onto a cross-linked ConA column;
(2) eluting bound protein from the column;
(3) adsorbing the eluate of step (2) onto a heparin-Sepharose ® column;
(4) eluting bound protein from the column of step (3); and
(5) chromatographing the eluate of step (4) on an RP-HPLC column using a trifluoroacetic acid-acetonitrile system, and recovering the substantially pure osteogenically active protein composition as the fraction eluting from the column at approximately 42–45% acetonitrile.

Further characterization of the osteogenic protein of this invention may be carried out using procedures known in the art. Its isoelectric focusing pattern, isoelectric point, susceptibility to degradation by proteases or other chemicals such as acids or bases, and affinity to other materials such as other lectins, and the like may be determined using means known in the art. For purified proteins, the weight ratio of osteogenic protein to carrier to be used in the method of preparing the invention will be in the range of about 1:5,000 to 1:50,000.

Initial tests of the osteogenic protein composition indicate that it is preferable, in the concentrations and formulations tested, to coadminister a cofactor protein having TGF-beta activity to achieve bone induction at nonbony sites. In this regard, TGF-beta (TGF-beta1, TGF-beta2, other members of the TGF-beta family, and mixtures thereof) may enhance the process of bone induction through ancillary activities such as antiinflammatory activity, chemotactic activity, and the like. Other molecules that exhibit such activities may also be useful as co-factors for bone induction. The cofactor protein may, of course, be active at other concentrations or in other formulations. Further, it may not be necessary to coadminister TGF-beta at bony sites, since the amount of endogenous TGF-beta present at the site of action may be sufficient. The weight ratio of osteogenic protein to TGF-beta in the composition will usually be in the range of about 10:1 to 1:10.

Methods for preparing TGF-betas are described in U.S. Pat. No. 4,774,322, issued Sep. 27, 1988, which is incorporated herein by reference.

The osteogenic protein of the invention will normally be formulated in osteogenically effective amounts with pharmaceutically acceptable solid or fluid carriers. Preferably, the formulations include a matrix that is capable of providing a structure for developing bone and cartilage. Potential matrices may be biodegradable or nonbiodegradable, and may be chemically or biologically defined.

A preferred pharmaceutically acceptable carrier is purified atelopeptide collagen. Commercial preparations of such collagen may be obtained from Collagen Corporation, Palo Alto, Calif., under the trademark Vitrogen ® 100 collagen in solution (CIS). The requirements for the collagen preparation used to deliver the osteogenic protein are merely that the collagen be non-immunogenic, preferably atelopeptide collagen, which is uncontaminated with noncollagenous materials. In a preferred embodiment, the collagen in solution concentration to be used in the processing of the invention will be in the range of about 1–10 mg/ml, most preferably about 3 mg/ml. The CIS may be reconstituted with a phosphate buffer to provide a fibrillar collagen carrier. A presently preferred composition contains approximately 65 mg/ml fibrillar collagen.

Other preferred pharmaceutically acceptable carriers may be materials such as calcium sulfate, hydroxyapatite, tricalcium phosphate, polyorthoesters, polylactic-polyglycolic acid copolymers, bioglass, and the like.

A.3. Preparation of Osteoinductive Prosthesis

A number of procedures may be used to combine the stress-bearing member with an osteoinductive composition. The simplest procedure is to coat or dip the stress-bearing member with a solution of OFE, or a suspension containing the osteogenic protein and TGF-beta. Sufficient OFE or suspension of the osteogenic protein and TGF-beta is applied to completely cover the portion of the stress-bearing member to be fixed by bone ingrowth. Alternatively, sufficient amounts of the osteoinductive composition may be applied to completely saturate the stress-bearing member.

In a preferred embodiment, a solution of OFE or a suspension containing the osteoinductive protein and TGF-beta may be applied to the stress-bearing member by vacuum force. In practice, the OFE or osteoinductive suspension is homogeneously dispersed into the pores of the stress-bearing member. Vacuum force is preferred to positive mechanical force, (e.g., from pushing or packing the material into pores) to prevent separation of water from the solution or suspension. Excessive vacuum will cause similar undesireable results. The presently preferred degree of vacuum is about 0.1–1 atm, most preferably about 0.5 atm. An exemplary method is as follows:

A porous stress-bearing member is placed on a stainless screen glass filter holder (Millipore, Mass.) which is attached to a vacuum line. A suspension of osteoinductive protein and TGF-beta is placed on top of the stress-bearing member. The osteoinductive suspension is then drawn into the pores of the implant at a pressure of less than 1 atm, resulting in a homogeneously dispersed osteoinductive suspension in the pores of the stress-bearing member. The coated porous implant is then dried at 37° C. to less than 1% moisture by weight. The dry coated porous implant may then be assembled with a non-porous stress-bearing member to provide an effective osteoinductive prosthesis.

The solution of OFE or suspension containing the osteoinductive protein and TGF-beta may be further air-dried or freeze-dried onto the stress-bearing member to provide a dry osteoinductive prosthesis. An exemplary method is as follows:

(1) dissolving the OFE described above in HCl (pH 2.0) to obtain a solution containing 0.5–1 mg/ml OFE;
(2) sterile filtering the OFE solution through a 0.2 μm filter;
(3) mixing the OFE solution with collagen in solution (CIS);
(4) precipitating the OFE/CIS mixture with 0.02M $Na_2HPO_4$, pH 7.2, overnight at ambient temperature to obtain an OFE/fibrillar collagen (FC) precipitate;
(5) centrifuging the precipitate to obtain an OFE/FC pellet;
(6) adjusting the concentration of the OFE/FC pellet with phosphate-buffered saline;
(7) coating a porous implant with the resulting dispersion from step 6; and (8) drying the coated porous implant at 37° C. to dryness (less than 1% moisture by weight).

An alternative processing method is to prepare an air-dried or freeze-dried osteoinductive composition in the form of a membrane or sheet which is then wrapped around the stress-bearing member. A preferred method for preparing such a membrane is by combining the OFE or a suspension containing the osteoinductive protein and TGF-beta with a purified collagen preparation and processing the composition as described in U.S. Pat. No. 4,600,533, issued Jul. 15, 1986, or U.S. Pat. No. 4,689,399, issued Aug. 25, 1987, or U.S. Pat. No. 4,725,671, issued Feb. 16, 1988.

Another alternative processing method is to prepare the osteoinductive composition in a ceramic carrier as described in U.S. Pat. No. 4,563,350, issued Jan. 7, 1986, packing the resultant osteoinductive particles into the gaps between the stress-bearing member and host tissue at the time of surgery.

A.4. Implantation

Implantation of the osteoinductive prosthesis of the invention employs techniques appropriate for the particular defect to be remedied. These procedures are those ordinarily used in the art and do not form part of the invention.

B. Examples

The following examples are intended to illustrate but not to limit the invention.

B.1. Preparation of a Porous Titanium Implant with Osteoinductive Proteins a. Purified OFE was prepared by extracting demineralized bone with a chaotropic extractant, subjecting the extract to gel filtration to recover a fraction containing proteins of molecular weight 10–30 Kd, adsorbing the fraction onto a CMC-cation exchanger at approximately pH 4.5–5.5, and eluting the purified extract from the cation exchanger with a NaCl gradient of about 10 mM to about 150 mM.

b. 15 mg by dry weight of the OFE prepared in B.1.a. was dissolved in 15 ml HCl (pH 2.0) to obtain an OFE solution of about 1 mg/ml OFE. The resulting solution was sterile filtered with a 0.2 μm filter.

c. The sterile filtered OFE solution from B.1.b. was mixed with 150 ml of 3 mg/ml collagen in solution (CIS) to obtain a 165 ml OFE/CIS mixture. The mixture was precipitated with 0.02M $Na_2HPO_4$, pH 7.2, at ambient temperature (20° C.) overnight to provide an OFE/fibrillar collagen (FC) dispersion.

d. The OFE/FC dispersion of B.1.c. was centrifuged at 13,000×g for 20 min to obtain an OFE/FC precipitate.

e. Phosphate-buffered saline was added to the precipitate of B.1.d. to adjust the total protein concentration to 65 mg/ml.

f. Approximately 40 μL of the OFE/FC dispersion of B.1.e. was used to coat the surface of a porous titanium disc measuring 1 cm in diameter by thickness, having a void volume of about 33%.

g. The resultant wet OFE/FC/titanium implant comprised approximately 80 μg OFE and 2.5 mg FC per implant.

h. The wet OFE/FC/titanium implant was incubated and dried at 37° C. to dryness (less than 1% moisture by weight).

B.2. Implantation of a Porous Titanium Implant with Osteoinductive Proteins a. Bony ingrowth of titanium implants was studied in the following experiment. The following implant formulations were first prepared as descried in B.1:

1. 2.5 mg FC, porous titanium disc measuring 1 cm diameter by 0.17 cm thickness, and having a void volume of approximately 33% (FC/titanium implant); and
2. 80 μg OFE, 2.5 mg FC, porous titanium implant as above (OFE/FC/titanium implant).

Twelve male Sprague-Dawley rats were used in this experiment, six rats per test group. The samples were surgically implanted into the thoracic subcutaneum of each rat, using standard procedures. Three explants were taken from each test group at days 14 and 28 for histological analysis.

At day 14, no cartilage or bone formation was observed with the FC/titanium implants. There was a low to moderate infiltration of fibrous connective tissue into the pores of the titanium implant and a small number of macrophages present. No giant cells were present.

The explants containing OFE/FC/titanium implants showed moderate to good calcifying cartilage formation and low to moderate bone formation on the surface of the implants. There was moderate to good infiltration of fibrous connective tissue into some of the pores of the titanium implant, and a small number of macrophages, PMNs, and eosinophils present. No giant cells were present.

By day 28, there was still no cartilage or bone formation with the FC/titanium implants; however, there was good to excellent infiltration of fibrous connective tissue into the pores of the titanium implant. There was no change in the number of macrophages. PMNs and eosinophils had disappeared.

The explants containing OFE/FC/titanium implants showed mature bone with all of the cartilage seen at day 14 replaced by bone at day 28. Good connective tissue and moderate bone ingrowth into most or all of the titanium pores were observed. No inflammatory or giant cells were detected in these explants by histological evaluation.

We claim:

1. A method for permanently fixing a stress-bearing bone-replacement prosthesis having a stress-bearing member by inducing bony ingrowth into the stress-bearing member, where said prosthesis is implanted in a site in a subject, wherein said method comprises:
    administering to the site in the subject a substantially pure osteogenically active protein and an effective amount of a transforming growth factor of the beta type in a pharmaceutically acceptable carrier wherein the osteogenic protein and carrier are present in a weight ratio of about 1:5,000 to 1:50,000.

2. The method of claim 1 wherein the osteogenic protein and transforming growth factor of the beta type are present in a weight ratio of about 10:1 to 1:10.

3. The method of claim 1 wherein the pharmaceutically acceptable carrier comprises collagen.

4. The method of claim 1 wherein the pharmaceutically acceptable carrier is a ceramic.

5. The method of claim 4 wherein the ceramic is selected from the group consisting of hydroxyapatite, tricalcium phosphate, and a mixture thereof.

6. A method for repairing bone defects comprising:
    administering to a site of a bone defect a bone replacement composition comprising a substantially pure osteogenically active protein and an effective amount of transforming growth factor of the beta-type in a pharmaceutically acceptable carrier, and a stress-bearing member wherein the osteogenic protein and carrier are present in a weight ratio of about 1:5,000 to 1:50,000.

7. The method of claim 6 wherein the stress-bearing member is comprised of a material selected from the group consisting of titanium, stainless steel, an alloy containing titanium, cobalt, chromium, and molybdenum.

8. The method of claim 6 wherein the osteogenic protein and transforming growth factor of the beta type are present in a weight ratio of about 10:1 to 1:10.

9. The method of claim 6 wherein the pharmaceutically acceptable carrier comprises a ceramic.

10. The method of claim 6 wherein the pharmaceutically acceptable carrier comprises a ceramic.

11. The method of claim 10 wherein the ceramic is selected from the group consisting of hydroxyapatite, tricalcium phosphate, and a mixture thereof.

12. A method for fixing a stress-bearing bone-replacement prothesis to a bone, comprising the steps of:
 implanting the stress-bearing bone-replacement prothesis in a patient so as to contact bone of the patient wherein transforming growth factor of the beta type and osteogenic factor extract are in a pharmaceutically acceptable carrier and are homogeneously dispersed into pores of the prothesis; and
 allowing the prothesis to remain in contact with the bone until bone growth into the pores occurs fixing the prothesis to the bone wherein the osteogenic factor extract and transforming growth factor of the beta type are present in a weight ratio of 10:1 to 1:10.

* * * * *